United States Patent
Assadi et al.

(10) Patent No.: US 10,266,440 B2
(45) Date of Patent: Apr. 23, 2019

(54) ANAEROBIC DIGESTION SYSTEM AND METHOD

(71) Applicants: Abdolreza Assadi, Minnetonka, MN (US); Ronald Scott Sleight, Manitowish Waters, WI (US)

(72) Inventors: Abdolreza Assadi, Minnetonka, MN (US); Ronald Scott Sleight, Manitowish Waters, WI (US)

( * ) Notice: Subject to any disclaimer, the term of this patent is extended or adjusted under 35 U.S.C. 154(b) by 0 days.

(21) Appl. No.: 15/639,264

(22) Filed: Jun. 30, 2017

(65) Prior Publication Data

US 2018/0002206 A1    Jan. 4, 2018

Related U.S. Application Data

(60) Provisional application No. 62/357,413, filed on Jul. 1, 2016.

(51) Int. Cl.
*C02F 3/28* (2006.01)
*B09B 3/00* (2006.01)
(Continued)

(52) U.S. Cl.
CPC .............. *C02F 3/282* (2013.01); *B09B 3/00* (2013.01); *C02F 1/68* (2013.01); *C02F 3/286* (2013.01); *C02F 3/341* (2013.01); *C02F 9/00* (2013.01); *C12P 5/023* (2013.01); *D21B 1/026* (2013.01); *D21C 5/02* (2013.01); *D21C 11/125* (2013.01); *D21C 11/127* (2013.01); *C02F 1/38* (2013.01);
(Continued)

(58) Field of Classification Search
CPC ...... C02F 3/282; C02F 3/341; C02F 2303/10; C02F 2303/26; C02F 2103/20; C02F 1/38; C02F 11/04; C02F 3/284; C02F 1/66; C02F 2301/046; C02F 2103/08; C02F 1/68; C02F 9/00; C02F 3/286; D21B 1/026; C12P 5/023; D21C 11/125; D21C 11/127; D21C 5/02; B09B 3/00
USPC .............................. 210/603, 173, 252, 259
See application file for complete search history.

(56) References Cited

U.S. PATENT DOCUMENTS 4,610,792 A    9/1986 Van Gils et al.
4,889,626 A   12/1989 Browne
(Continued)

FOREIGN PATENT DOCUMENTS

EP    0135486    3/1985
EP    0951934    10/1999
(Continued)

OTHER PUBLICATIONS

International Search Report and Written Opinion for PCT Application No. PCT/US2017/040327 dated Sep. 20, 2017 (12 pages).
(Continued)

*Primary Examiner* — Fred Prince
(74) *Attorney, Agent, or Firm* — Schwegman Lundberg & Woessner, P.A.

(57) ABSTRACT

An anaerobic digestion system may include a material grinding/pulping portion, a hydrolysis portion arranged downstream of the grinding portion, a multiple chamber anaerobic reactor arranged downstream from the hydrolysis portion and including a gas collection and reintroduction system, a collection system for collecting digestate and gas from the anaerobic reactor.

20 Claims, 16 Drawing Sheets

(51) Int. Cl.
*C02F 9/00* (2006.01)
*D21C 5/02* (2006.01)
*D21C 11/12* (2006.01)
*C02F 1/68* (2006.01)
*C02F 3/34* (2006.01)
*C12P 5/02* (2006.01)
*D21B 1/02* (2006.01)
*C02F 1/38* (2006.01)
*C02F 1/66* (2006.01)
*C02F 11/04* (2006.01)
*C02F 103/08* (2006.01)
*C02F 103/20* (2006.01)

(52) U.S. Cl.
CPC ............... *C02F 1/66* (2013.01); *C02F 3/284* (2013.01); *C02F 11/04* (2013.01); *C02F 2103/08* (2013.01); *C02F 2103/20* (2013.01); *C02F 2301/046* (2013.01); *C02F 2303/10* (2013.01); *C02F 2303/26* (2013.01)

(56) References Cited

U.S. PATENT DOCUMENTS

| | | | |
|---|---|---|---|
| 5,217,899 A | | 6/1993 | Shapiro et al. |
| 5,377,917 A | * | 1/1995 | Wiljan ............ C05F 9/02 241/14 |
| 6,254,775 B1 | * | 7/2001 | McElvaney ...... C02F 3/103 210/603 |
| 9,926,212 B2 | | 3/2018 | Davie et al. |
| 2002/0079266 A1 | | 6/2002 | Ainsworth et al. |
| 2008/0193994 A1 | | 8/2008 | Choate et al. |
| 2009/0095673 A1 | | 4/2009 | Choate et al. |
| 2009/0107917 A1 | | 4/2009 | Capehart |
| 2012/0156744 A1 | * | 6/2012 | Macdonald ........ C02F 3/286 435/155 |
| 2013/0126426 A1 | | 5/2013 | Jones et al. |
| 2013/0193069 A1 | | 8/2013 | Aiken et al. |
| 2013/0260433 A1 | * | 10/2013 | Zhang ............. C02F 3/286 435/167 |
| 2014/0072994 A1 | | 3/2014 | Pidaparti et al. |
| 2014/0260464 A1 | * | 9/2014 | LeSueur ........... C05F 17/00 71/9 |
| 2016/0030891 A1 | | 2/2016 | Oskoui |
| 2016/0230193 A1 | * | 8/2016 | Josse ............... C02F 9/00 |
| 2017/0073586 A1 | * | 3/2017 | Iversen ........... C10G 1/008 |

FOREIGN PATENT DOCUMENTS

| | | |
|---|---|---|
| EP | 2638940 | 9/2013 |
| JP | H03224621 | 10/1991 |
| JP | H10174986 | 6/1998 |
| JP | 2009066503 | 4/2009 |

OTHER PUBLICATIONS

International Search Report and Written Opinion for related PCT Application No. PCT/US2015/043167 dated Dec. 23, 2015 (17 pages).

* cited by examiner

FIG. 4 ↗ 134

ANAEROBIC DIGESTION SYSTEM AND METHOD

CROSS-REFERENCE TO RELATED APPLICATIONS

The present application claims priority to U.S. Provisional Application No. 62/357,413, entitled Anaerobic Digestion System and Method, and filed on Jul. 1, 2016, the content of which is hereby incorporated by reference herein in its entirety.

FIELD OF THE INVENTION

The present disclosure relates to processing and/or treatment of solid and liquid wastes. In particular, the present disclosure relates to an improved anaerobic digestion system and method for processing solid and liquid wastes. Still more particularly, the present application relates to an anaerobic digestion system that includes a mechanism for increasing the surface area of the waste prior to processing, a catalyst, a gas collection and reintroduction system, and a fluid source including waste water such as animal manure and/or human waste water from a sanitary sewer or septic tank, for example.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

In one or more embodiments, an anaerobic digestion system may include a material grinding portion and a hydrolysis portion arranged downstream of the grinding portion. The system may also include an anaerobic reactor arranged downstream from the hydrolysis portion. The anaerobic reactor may include a gas collection and reintroduction and polishing system. The system may also include a collection system for collecting digestate and gas from the anaerobic reactor.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present application, in some embodiments, relates to processing solid and liquid wastes such as woody wastes, animal waste, and other feedstock materials. In one or more embodiments, the system may include an improved anaerobic digestion process that incorporates the use of waste water or other liquid wastes. The system may include a pulping and/or grinding system that reduces the material particle size of the incoming feedstock so as to increase the surface area of the material and improve the efficiency of the system. The system may also include a gas collection and reintroduction system in an anaerobic reactor that creates an environment to more efficiently utilize the bacteria or other microorganism activity in the anaerobic portion of the process. The system may include a gas collection system where the produced gas may be collected and used for energy generation in one or more forms. Still further, the system may be used in conjunction with water filtration systems such as those described in U.S. patent application Ser. No. 14/815,130 entitled Single-Stage Water Treatment System filed on Jul. 31, 2015 to provide effluent water that may be used for several purposes and may even be potable. The system may, thus, provide an improved system for converting waste to energy while supplying useable end products such as solid digestate for use as a soil conditioner or fertilizer, liquid digestate for use as liquid fertilizer, and water suitable for several uses including irrigation, drinking water, and other uses.

Figure 1:
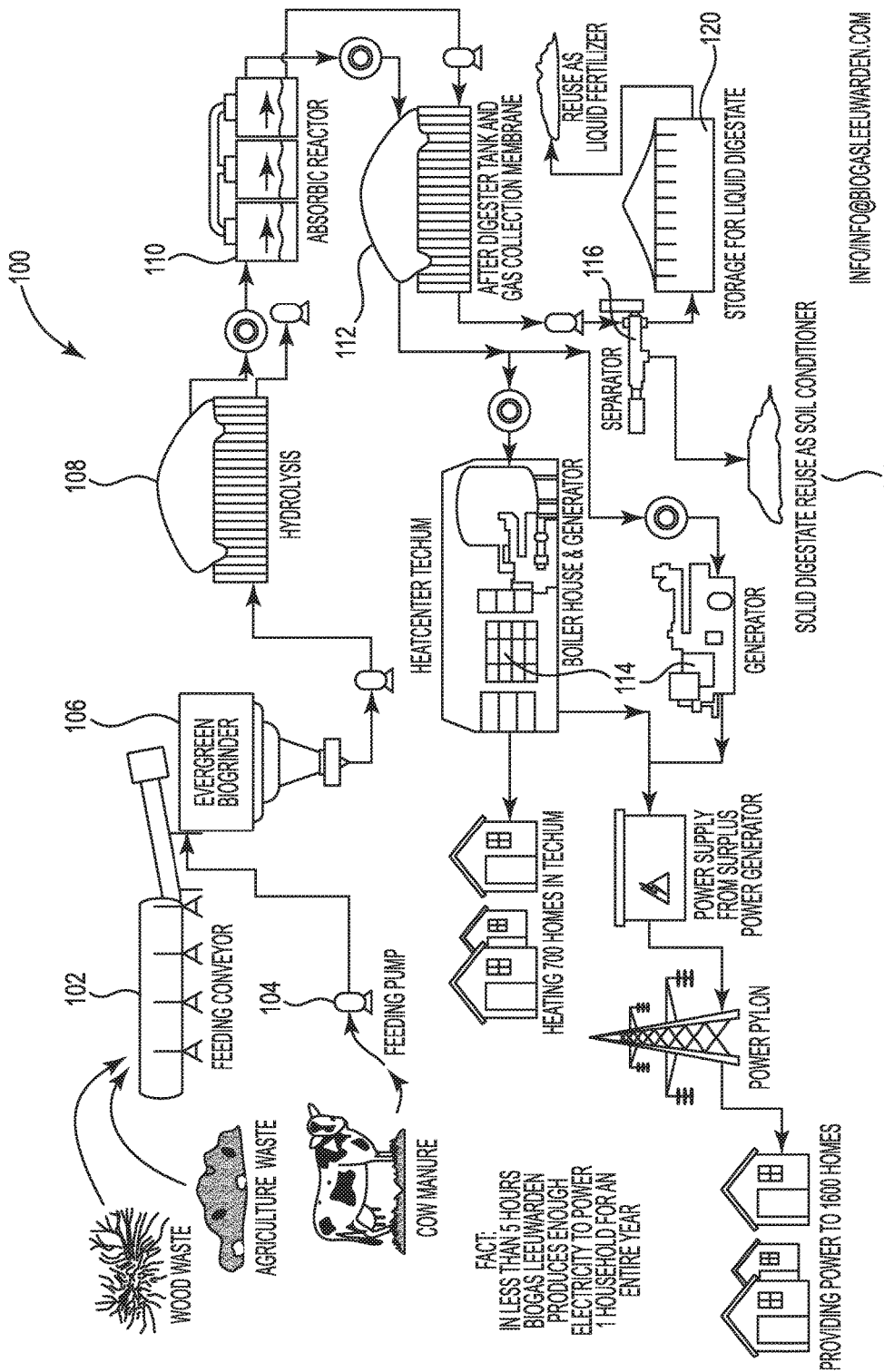
FIG. 1 is a schematic diagram of a digestion system, according to one or more embodiments.

Turning now to FIG. 1, the system 100 may include one or more input devices such as a feeding conveyor 102 and a feeding pump 104. The system may also include a pulping and/or grinding device 106, a hydrolysis portion 108, an anaerobic reactor 110, a collection system 112, one or more generators 114, a separator 116, a solid digestate collection area or portion 118, and a liquid digestate collection area or portion 120. As suggested, the system 110 may be used to process solid waste feedstocks to create effluent useable gas and other useable solid and liquid effluents.

As shown in FIG. 1, the input devices may include a feeding conveyor 102 and a feeding pump 104. The feeding conveyor 102 may be configuring for transporting solid feed stock material such as woody wastes, agricultural waste, trash or the organic portion of municipal solid waste including paper and/or cardboard, or other solid waste materials from a holding or staging area to the pulping or grinding device or system. The feeding conveyor 102 may include one or more conveying systems used in series or parallel such as belt-type conveyors, auger conveyors, shaker conveyors, paddle conveyors or other devices for continuously or intermittently moving material along a path from the holding or staging area to the pulping or grinding device or system 106. The feeding conveyor 102 may have a loading end positioned at or near ground level to allow for easily moving material from the staging area onto the conveyor. In some embodiments, an input hopper may be provided allowing for material to be loaded and continuously or intermittently dropped onto the loading end of the conveyor. In other embodiments, a backhoe, front-end loader, or other device may be used to lift feed stock material onto the conveyor. Still other systems and method for loading feedstock material onto the conveyor may be provided. The conveyor may also include an unloading end that may be positioned at or near and/or above the pulping/grinding system 106 such that material from the conveyor 102 may be offloaded from the conveyor by freefalling into the pulping/grinding device or system. In one or more embodiments, the unloading end may be positioned to drop or offload the material onto an elevator or other moving device to pass the material from the conveyor to the pulping/grinding system 106.

The other input device may be in the form of a feeding pump 104 for pumping and/or moving liquid material from a tank or other holding area to the pulping/grinding device 106. The feeding pump 104 may be a sewage ejector type pump or system such as a grinding and pumping type pump used for lift stations and the like. The feeding pump may be in liquid communication with a supply tank or holding area so as to suck liquid from the supply tank or holding area and pump it to the pulping/grinding system 106 of device. The liquid communication may be provided by one or more systems of pipes or conduits having a submerged or otherwise accessible input end and an output end arranged to allow the liquid to be pumped into the pulping/grinding system.

The pulping/grinding system 106 may be configured to reduce the material particle size of the incoming feedstock and increase the surface area. Accordingly, the pulping/grinding system 106 may be configured to cut, slice, tear, and/or abruptly rip the material to annihilate and/or obliterate the structural integrity of the material placed therein. The pulping/grinding system may include a cutting/tearing mechanism in the form of a rotary-type blade and/or or paddle system for processing the incoming feedstock material. The cutting/tearing mechanism may be surrounded by a screen, mesh, or other device for maintaining larger portions of material at or near the cutting mechanism until they are small enough to pass through the screen or mesh. In some embodiments, the pulping/grinding system 106 may be the same or similar to a hydropulper, for example. In still other embodiments, a hammer mill 122 may be used. Still other mixing, blending, and/or processing systems and devices may be used.

Figure 2:
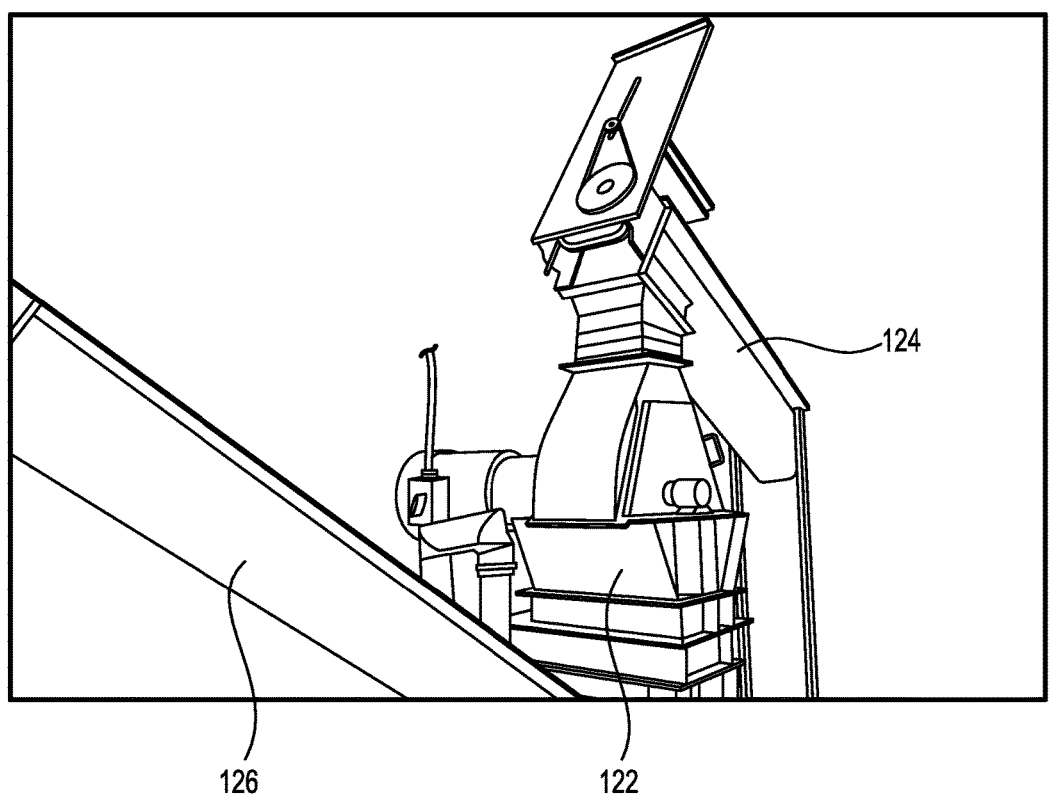
FIG. 2 is a perspective view of a hammer mill being used as a grinding/pulping portion of the system of FIG. 1, according to one or more embodiments.

One example of a hammer mill 122 being used to pulp/grind feedstock material is shown in FIG. 2. As shown, the hammer mill 122 may receive feedstock material from a conveyor 124, grind or pulp the material, and pass the material on with another conveyor 126. Still other arrangements of the pulping/grinding system 106 may be provided.

The pulping/grinding system 106 may include a skimmer for skimming out floating plastics or other light-weight materials. The skimmer may include a continuously rotating arm or paddle that collects the floating materials and collects them for transfer to other waste disposal and/or recycling operations.

The pulping system 106 may also include a sand/grit collection system in the base to collect heavy inert material. The sand/grit collection system may include a sediment removal system or other device to maintain the bottom of the tank and remove the sediment.

The pulping/grinding system 106 may include a catalyst input portion 128 to include a catalyst in the process. In some embodiments, the catalyst input portion 128 may include a nozzle, orifice, or other opening for continuous or intermittent feeding of the catalyst into the system. In some embodiments, portions of catalyst may be simply periodically or continuously dropped into an open top of the pulper/grinder. In some embodiments, the catalyst may include magnetite, tungsten, iron oxide, or aluminum oxide. Still other catalysts may be provided. The pulping/grinding system 106 may be in liquid communication with the hydrolysis portion and a pump may be provided for transferring material from the pulping/grinding portion to the hydrolysis portion.

Figure 3:
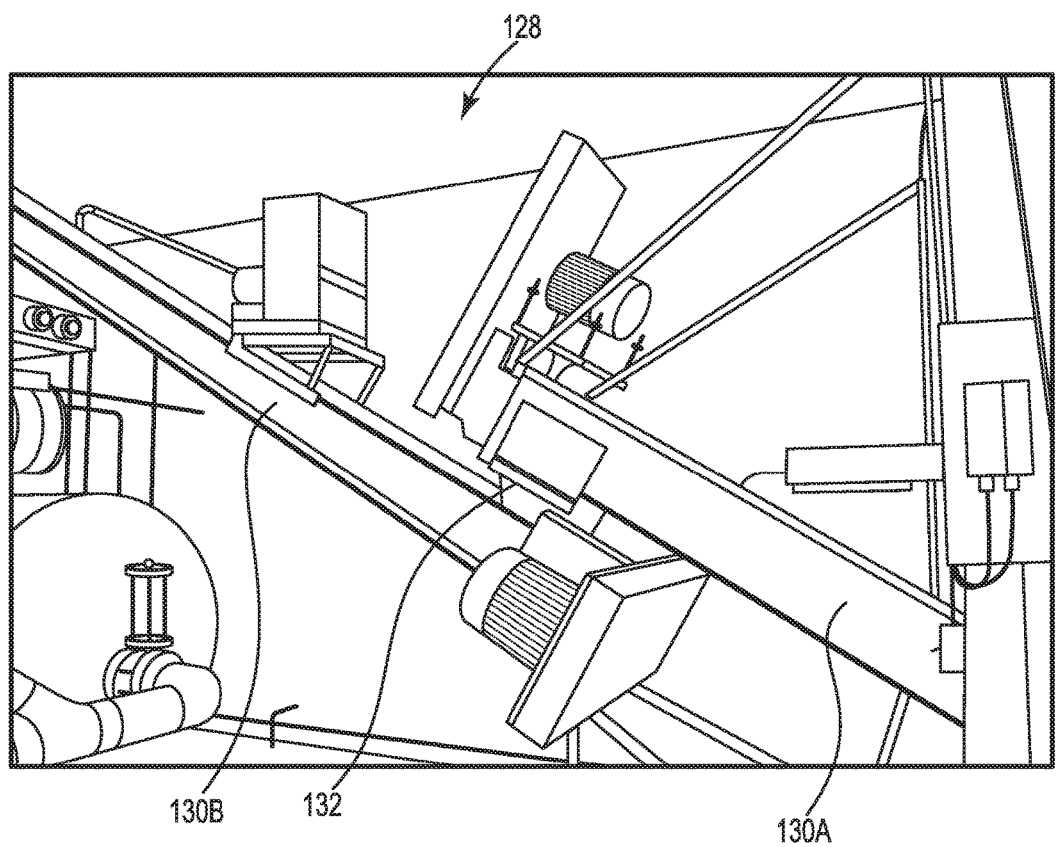
FIG. 3 is a perspective view of a catalyst adding portion of the system of FIG. 1, according to one or more embodiments.

One example of a catalyst input portion 128 is shown in FIG. 3. As shown, the catalyst input portion may include a transition between a pair of conveyors 130A/B where the material passes through a funnel mechanism 132. The catalyst may be added at the transition between the two conveyors 130A/B, for example. In this or other embodiments, the catalyst may be added along the conveyed stream of material through a sidewall of the conveyor, for example.

Figure 4:
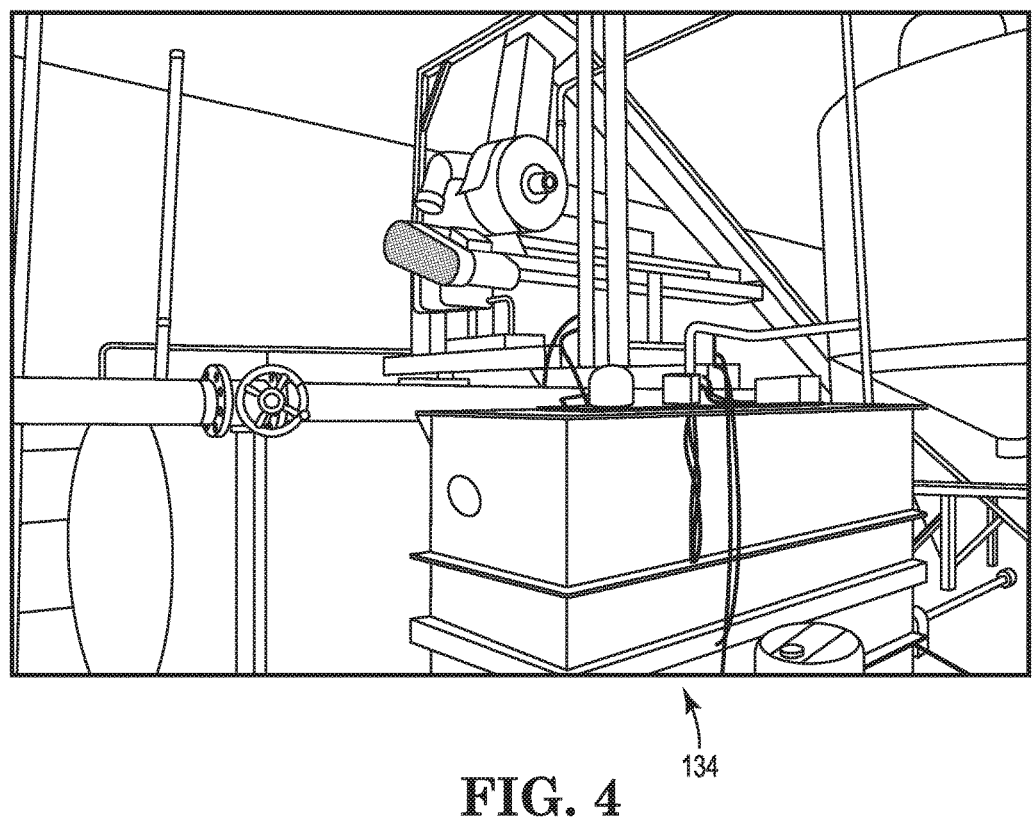
FIG. 4 is a perspective view of a conditioning system portion of the system of FIG. 1, according to one or more embodiments.
Figure 5:
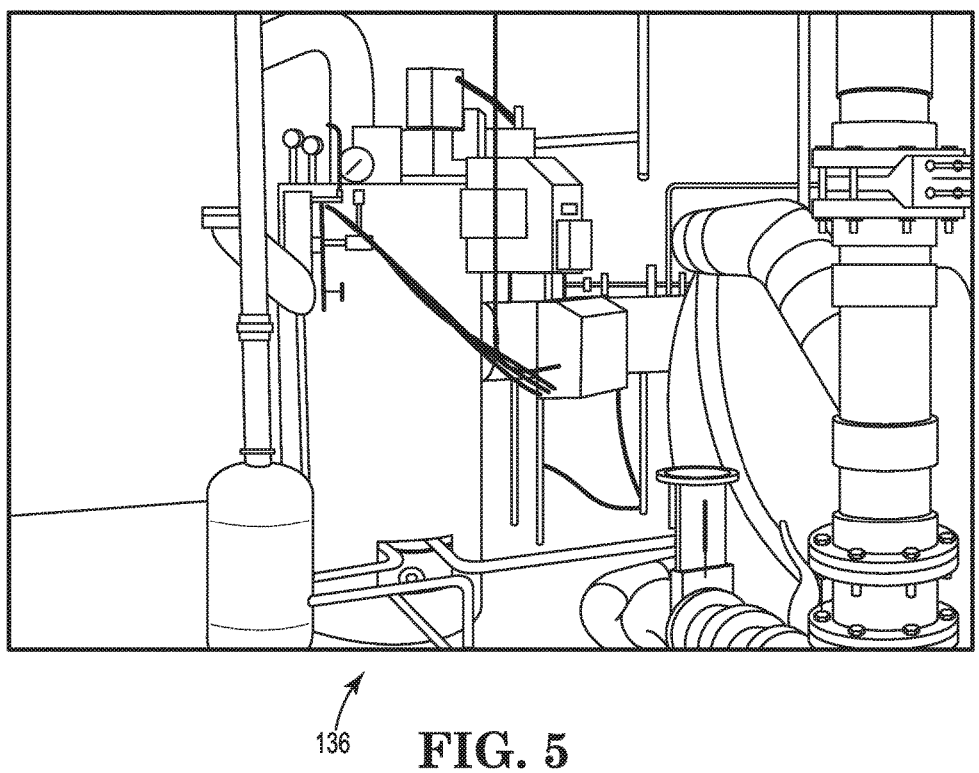
FIG. 5 is a perspective view of a steam boiler of the system of FIG. 1, according to one or more embodiments.

In some embodiments, prior to or in conjunction with the hydrolysis portion, a conditioning system 134 and boiler 136 may be provided to prepare the material for the hydrolysis stage. As shown in FIGS. 4 and 5, a conditioning system 134 and boiler 136 are shown, respectively.

Figure 6:
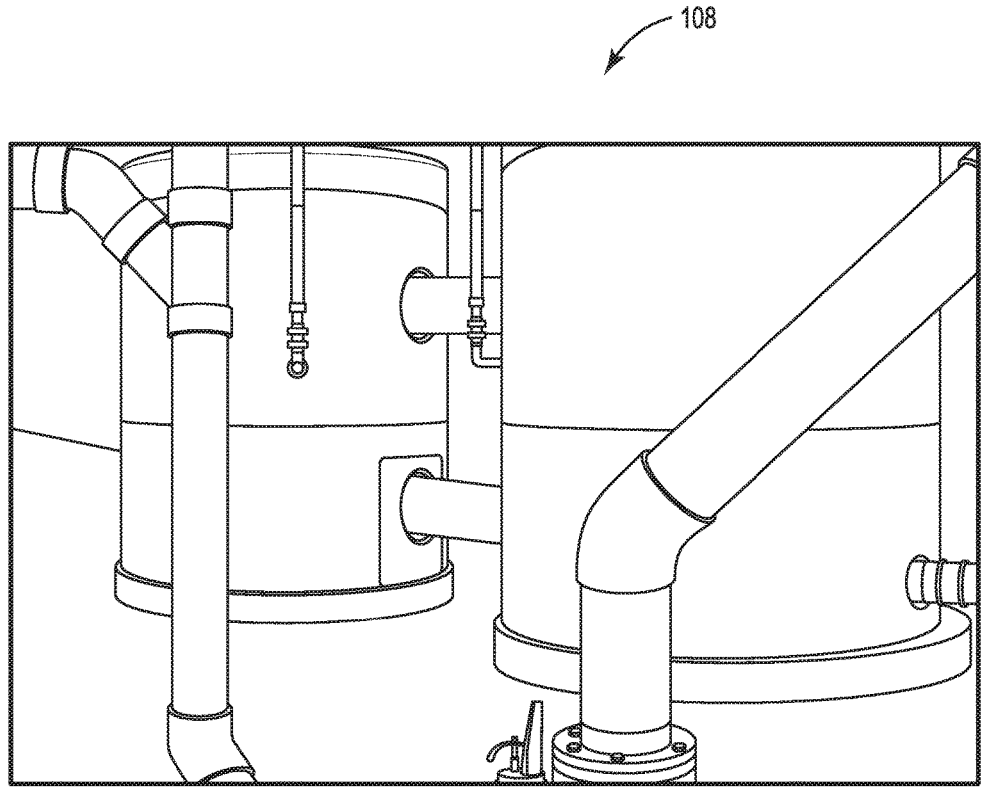
FIG. 6 is a perspective view of a hydrolysis portion of the system of FIG. 1, according to one or more embodiments.

As shown in FIG. 6, the hydrolysis portion 108 may be configured to receive the pulped and/or ground material from the pulper/grinder and begin hydrolysis. The hydrolysis portion may include a tank having a liquid holding portion and a gas collection area. The pulped/ground material may be pumped into the liquid holding portion where the hydrolysis process may be allowed to proceed. During this process, large polymers may be broken down to form amino acids, fatty acids, and simple sugars, for example. The production of organic acids may be closely monitored through pH and oxidation-reduction potential (ORP) measurements. In some embodiments, the tank may include a series of baffles or other flow control mechanisms to control the amount of time the liquid solution remains in the hydrolysis portion. During hydrolysis, the system may become anaerobic (without oxygen) to protect the oxygen intolerant methanogens in the digestion phase. In some embodiments, the tank used for the hydrolysis portion may be the same or similar to the tank used for the collection portion of the system.

The hydrolysis portion may include a liquid effluent exiting from the liquid holding portion and a gas effluent exiting from the gas collection area of the tank. These effluent portions may lead to the anaerobic reactor, which may include a series of anaerobic portions.

Figure 7:
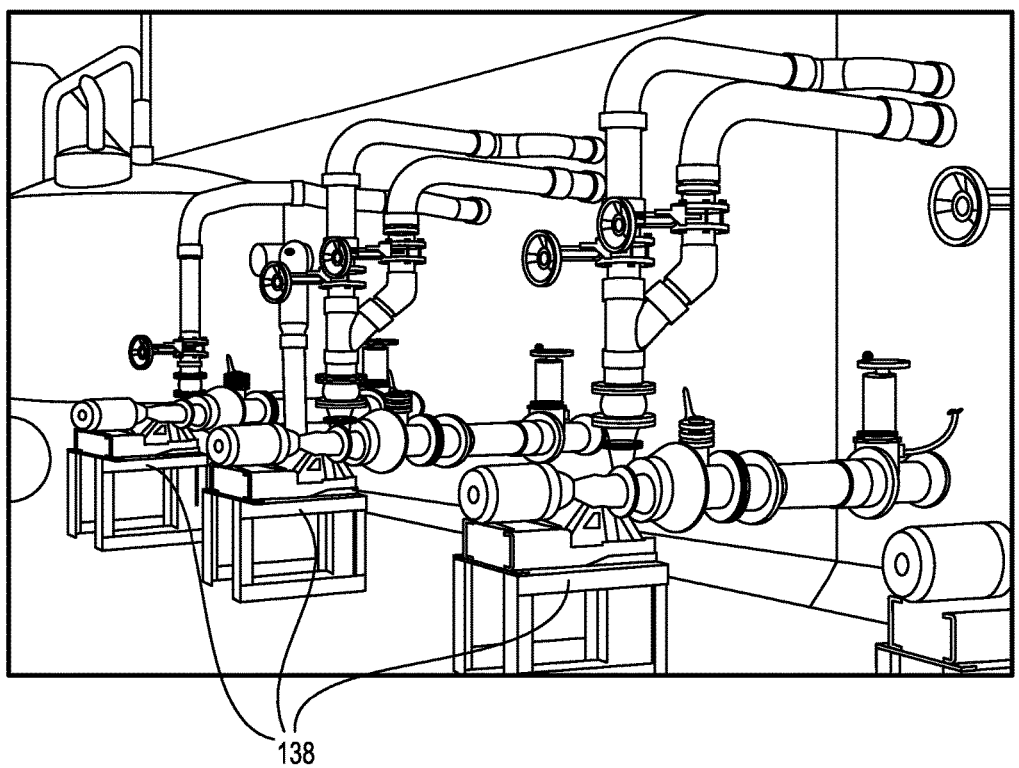
FIG. 7 is a perspective view of a series of agitators of the system of FIG. 1, according to one or more embodiments.

The anaerobic reactor 110 may include a series of compartments or processing sections or zones for performing one or more portions of an anaerobic digestion process. The anaerobic reactor 110 may include, for example, an acidogenesis compartment or zone, an acetogenesis compartment or zone, and a methanogenesis compartment or zone. These particular compartments or zones may be configured to consume and/or digest cellulosic structures that are very difficult to digest. Fewer or more compartments or zones may be provided in one or more embodiments. Each compartment or zone may include a reactor portion and a gas release area and the compartments or zones may be separated by baffles or other dividing mechanisms to control the time within which the material remains in a particular compartment. This dividing mechanism may control the time automatically or through a control mechanism. In some embodiments, the reactor may be designed as a plug-flow system where the flow of the material is regulated, automatically or by a control mechanism, to allow for volatile solid reduction and destruction of organic matter and conversion into biogas, particularly methane. Each reactor compartment may also include an agitator, mixer, or other mechanism 138 for continually or periodically mixing the material within the reactor compartment. An example of a series of agitators or mixers 138 is shown in FIG. 7 where the reactor compartments are on an opposite side of the concrete wall. Each reactor compartment may also be sealed off from the environment so as to maintain separation of the material in the reactor from the environment and, in particular, to maintain an absence of oxygen in the reactor or at least minimize or control the entry of oxygen into the system.

In the acidogenesis compartment, microorganisms may further break down the material after hydrolysis. The microorganisms in this compartment may be adapted to create an acidic environment and may cause the creation of ammonia, $H_2$, $CO_2$, $H_2S$, shorter volatile fatty acids, carbonic acids, and alcohols. The acidogenesis compartment may release gas from the liquid as the process is performed.

The acidogenesis compartment may be in liquid communication with the liquid effluent from the hydrolysis portion and may also be in fluid communication with the gas effluent from the gas collection area of the hydrolysis tank. In some embodiments, the gas from the hydrolysis tank may be perfused, bubbled, sparged, or otherwise re-entered into the liquid in the acidogenesis compartment. For example, the effluent gas from the hydrolysis tank may be contained within a pipe or other conduit that may extend into the reactor portion of the acidogenesis compartment and the conduit may include orifices or other openings allowing the gas to escape into the liquid within the reactor portion of the acidogenesis compartment. The effluent gas may include a pump/compressor to cause the gas to be at a higher pressure than the liquid in the reactor portion of the acidogenesis compartment allowing the gas to escape from the conduit and preventing liquid from entering the conduit. In some embodiments, the orifice or other openings may be arranged on a bottom side of the conduit to further resist the entry of liquid into the conduit.

In the acetogenesis compartment, acetate may be produced. That is, microorganisms may catabolize the components created in the acidogenesis compartment into acetic acid, $CO_2$, and $H_2$. Acetogens may break down the biomass such that methanogens can be used to create methane as biofuel. In the methanogenesis compartment, methane may be created by microbes know as methanogens.

The bioreactor may include a gas collection and reintroduction system for each compartment of the process that reintroduces the gas produced in the previous compartment into the reactor portion of the next compartment. That is, similar to the way the gas from the hydrolysis stage was described above as being reintroduced into the acidogenesis compartment, each stage of the bioreactor may include a similar mechanism. For example, the gas release area of the acidogenesis compartment may include an effluent that may pull the gas from the acidogenesis compartment and pump it or otherwise reintroduce it into the reactor portion of the acetogenesis compartment. The gas release area of the acetogenesis compartment may include an effluent that may pull the gas from the acetogenesis compartment and pump it or otherwise reintroduce it into the reactor portion of the methanogenesis compartment. This reintroduction of the released gas may be used as an agitation to mix the digester content and maintain the solid in suspension so as to allow the microorganisms to continue and/or better digest, consume, or otherwise reduce the organic and volatile material to produce biogas such as, for example, methane. In addition, this reintroduction may assist in polishing the carbon dioxide ($CO_2$) portion of the biogas and may assist in converting more $CO_2$ into methane. More particularly, the sparging of gas may introduce free carbon and free hydrogen into the liquid portion of the reactor allowing for the creation of more molecules of methane ($CH_4$). It is to be appreciated that reintroduction of the gas provided the above-mentioned unexpected result of producing more methane. That is, while reintroduction of the gas may help to agitate the fluid in the compartments and also maintain the microorganisms and material in suspension, it was not expected that such would result in the chemical reaction realized, which produces more methane. That is, other mixers such as mechanical mixers and augers may provide for agitation and maintenance of a suspension, but such methods do not produce the amount of methane production experienced by the present system.

In some embodiments, the anaerobic reactor may be a tank having the compartments discussed above arranged in linear series. That is, the tank may include generally rectangular compartments arranged in line with one another. In other embodiments, the tank may include a series of somewhat concentrically arranged compartments configured to route the material through the tanks in a spiral fashion. The concentrically arranged compartments may allow for an efficient use of space of the tanks and may provide for efficient reintroduction of the released gas into each compartment. The concentrically arranged compartments may be generally circular allowing for the hoop stresses present in the tank to be efficiently managed. Moreover, the concentric-type tank may be pre-fabricated and shipped to a site reducing and/or eliminating the need for onsite construction and/or fabrication.

Depending on the nature of the site on which the system is arranged, the anaerobic reactor may include an aboveground tank having a relatively high height of about 5-10 meters, or about 6-9 meters, or about 7 meters. In other embodiments, where space is not constrained or otherwise readily available, an under-ground tank may be provided with a height closer to about 1-6 meters, or about 3-5 meters, or about 4 meters. In the case of an above-ground tank, the tank may be insulated, whereas, in the case of an underground tank, the ground may provide the insulation. In some embodiments, the tank may be partially buried and the material excavated for the burial of the tank may be placed back around the tank to insulate the portion of the tank that extends above ground. Still other tank heights and sizes within or outside the ranges mentioned may be used.

Figure 8:
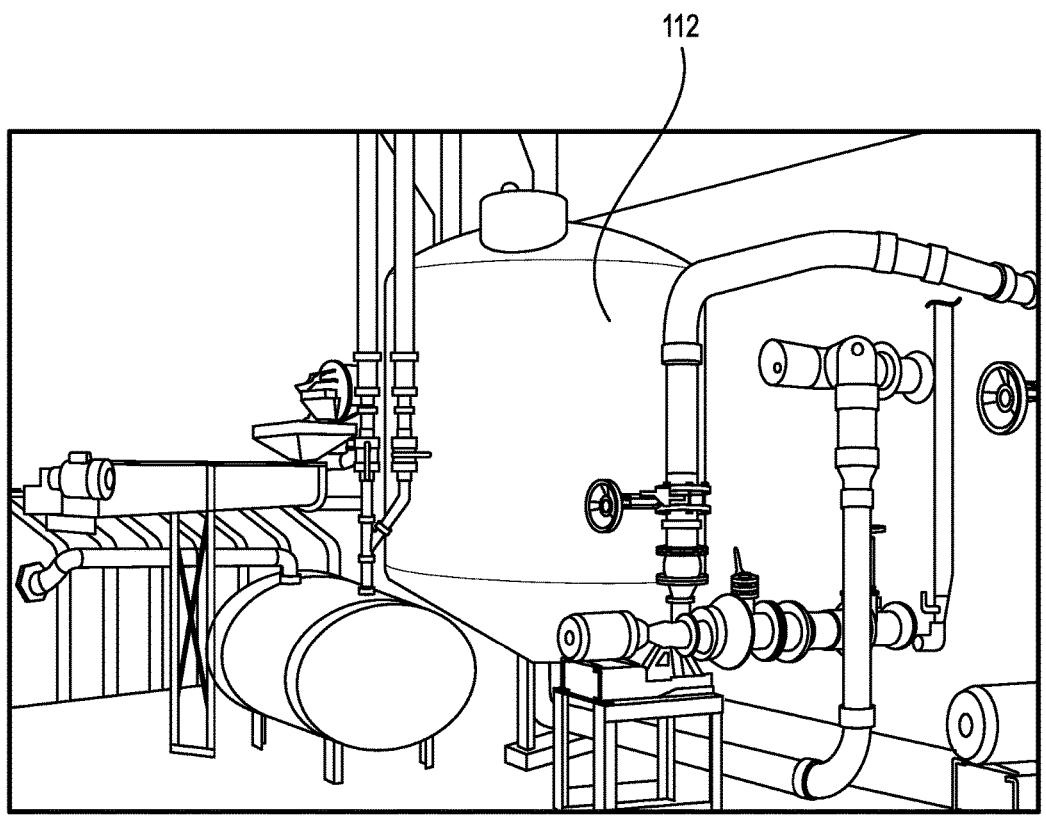
FIG. 8 is a perspective view of collection system of the system of FIG. 1, according to one or more embodiments.

As shown in FIG. 8, a collection system 112 may be configured to include a steel tank, concrete tank, or a tank of alternative construction defining a chamber for collecting the digestate and a gas collecting membrane. The tank may be in fluid communication with the last chamber of the anaerobic reactor and the digestate may be pumped into the tank portion of the collection system. The gas collecting membrane may define a space above the tank for collecting gas. The space above the tank may be in fluid communication with the gas release area of the last chamber in the anaerobic digester and the gas may be pumped into the space above the tank and within the gas collecting membrane. The gas collecting membrane may be resistant to hydrogen sulfide and may include a PVC-type cover having fungal and UV protections. In some embodiments, the collection system may be omitted or it may include a manifold system that directs the gas and the digestate from the reactor to particular location of use, for example.

Figure 9:
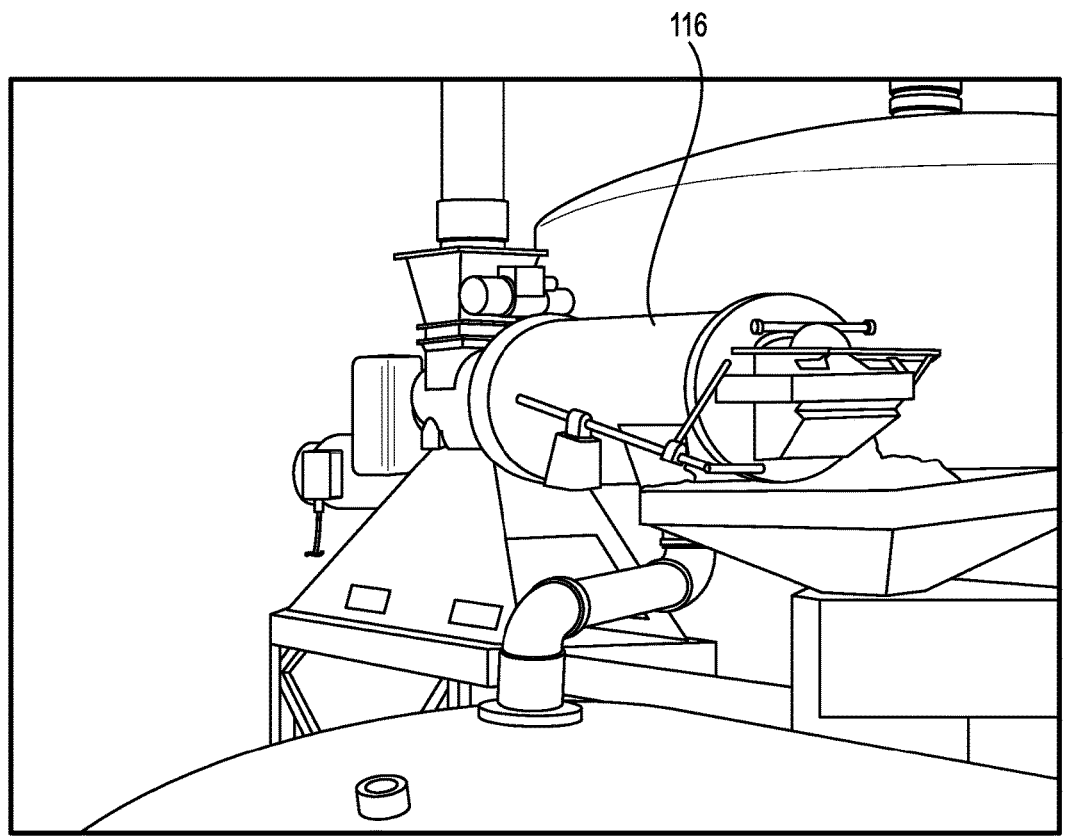
FIG. 9 is a perspective view of a separator of the system of FIG. 1, according to one or more embodiments.

As shown in FIG. 9, a separator 116 may be provided downstream from the collection system for separating the digestate into liquids and solids. The separator 116 may include a mesh system and an auger where the digestate is pumped into a cylindrical space defined by a mesh such that the liquid passes through the mesh and escapes the space, while the solids remain within the mesh. An auger within the mesh may compress the solids forcing additional liquid through the mesh and carrying the solids away along the cylindrical space to an exit. In other embodiments, a centrifuge-type separator may be provided. Still other types of separators may be used to separate liquids from solids.

The liquid from the separator may be routed to a liquid digestate collection area or portion. In one or more embodiments, the liquid digestate collection area or portion may include a storage tank for storing the liquid portion of the digestate. The liquid may be stored for later use as liquid fertilizer or for other uses. The liquid from the separator may also be dried and stored in a silo for later use. In one or more embodiments, the liquid concentrate may be stored for later use as a soil conditioner, fertilizer, or for other purposes.

In one or more embodiments, the liquid digestate may be further processed through a system similar to that described in U.S. patent application Ser. No. 14/815,130 entitled Single-Stage Water Treatment System and filed on Jul. 31, 2015, the content of which is hereby incorporated by reference herein in its entirety. In this embodiment, the liquid digestate may be used to produce water that is suitable for a variety of uses including cleaning, irrigation, drinking, and other uses.

Figure 10:
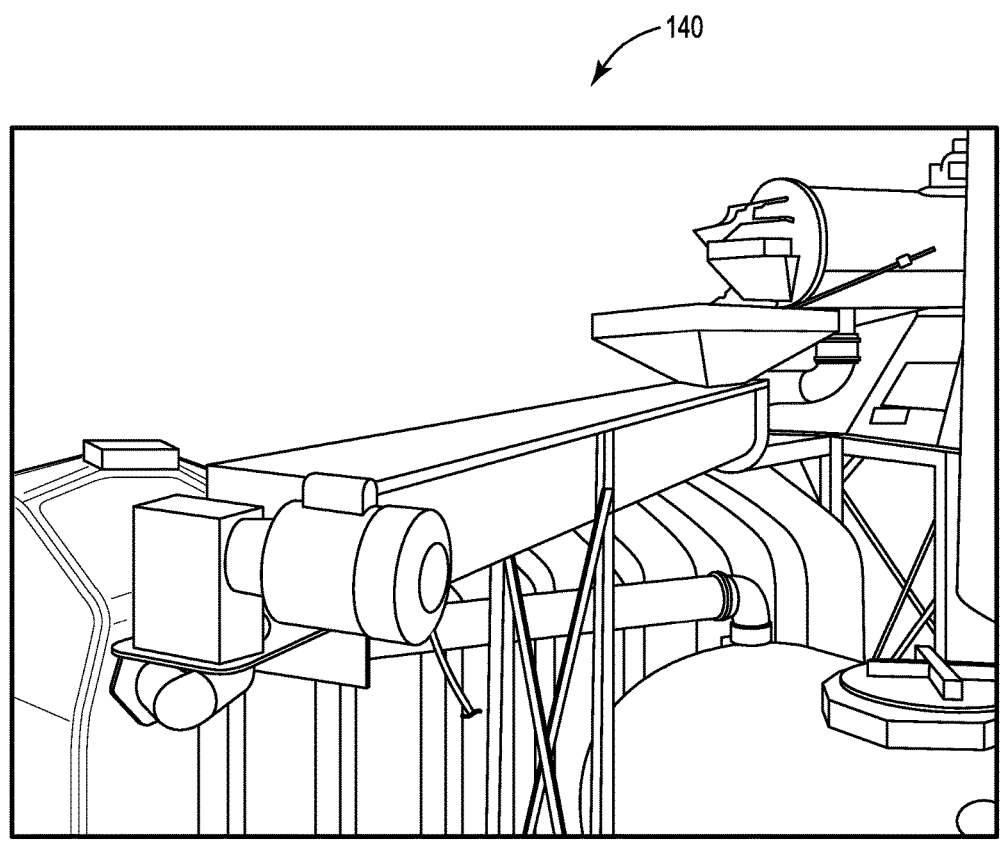
FIG. 10 is a perspective view of a fertilizer discharge system of the system of FIG. 1, according to one or more embodiments.

The solid material from the separator may exit the separator and fall or be carried away to a solid digestate collection area or portion. The solid digestate may be piled or heaped in a designated area on the ground or it may be placed in a tank or silo for later use. In one or more embodiments, the solid digestate may be stored for later use as a soil conditioner, fertilizer, or for other purposes. In some embodiments, the solids may be dried to create a class A fertilizer, which can be bagged and utilized as organic fertilizer. In one or more embodiments, a fertilizer discharge 140 may be provided as shown in FIG. 10, for example.

Returning to the collection system arranged downstream from the anaerobic reactor, the collected gas may be used in a variety of ways. In one or more embodiments, the gas may be provided to a generator where the gas may be used as fuel to run the generator and generate electricity. The electricity may be provided to the grid and may, thus, be routed to homes, businesses, or other users for consumption. In one or more other embodiments, the gas may be provided to a boiler house and used as fuel to generate heat such as by heating a boiler. The gas may be used directly to heat the liquid in the boiler and a generator may be provided for powering other aspects of the heating facility, for example. The liquid heated by the boiler may be used to heat homes, businesses, or other users. In some embodiments, the heated liquid may generate steam, which may be transported to users for use to generate heat. In some embodiments, the gas may be cleaned to pipeline quality and sent directly into the pipeline/grid to be sent to final users (homes or businesses) for various use such as heat or conversion to power.

Figure 15A:
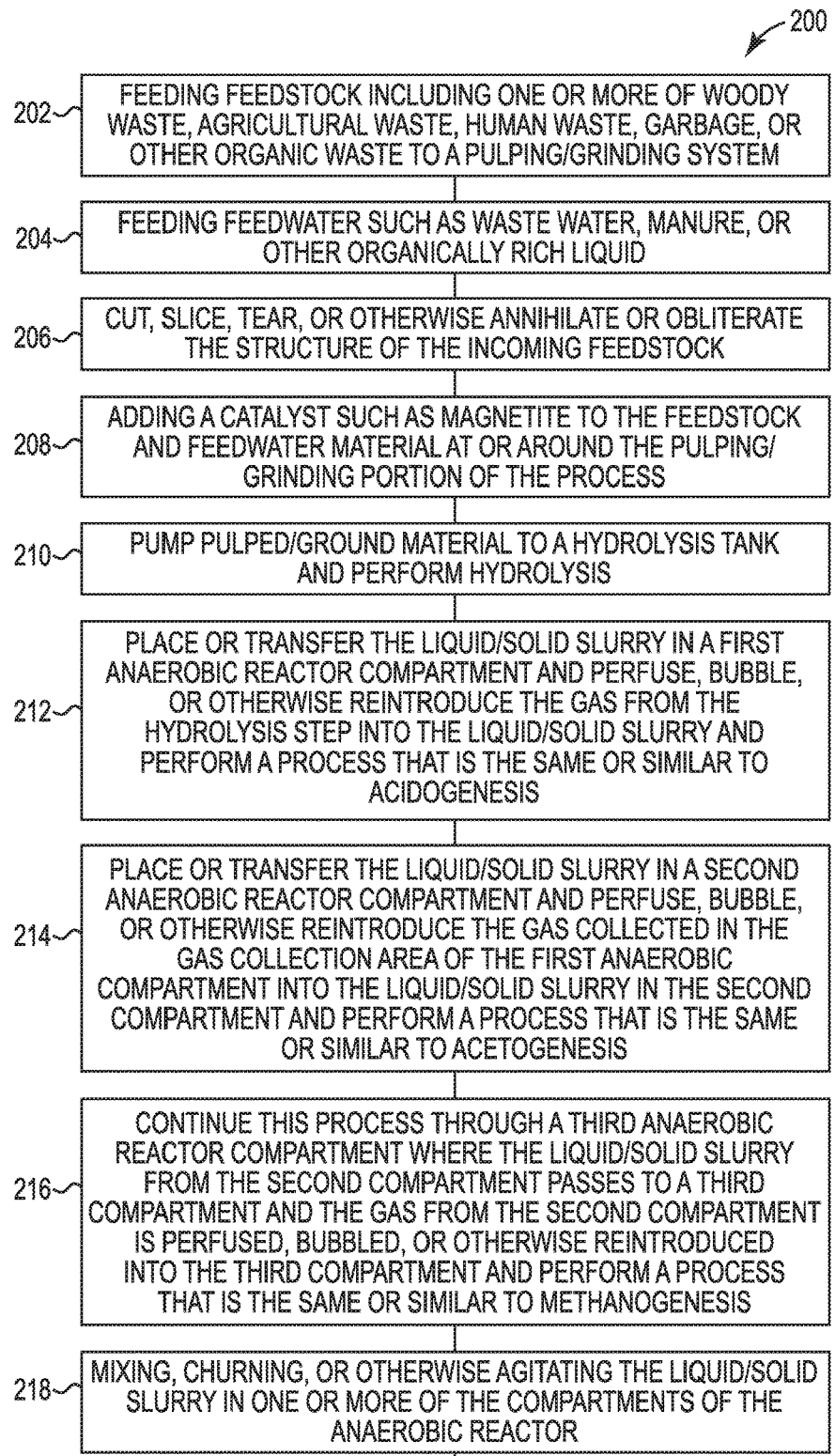
FIG. 15A is a partial flow diagram of a method for performance by the system of FIG. 1, according to one or more embodiments.
Figure 15B:
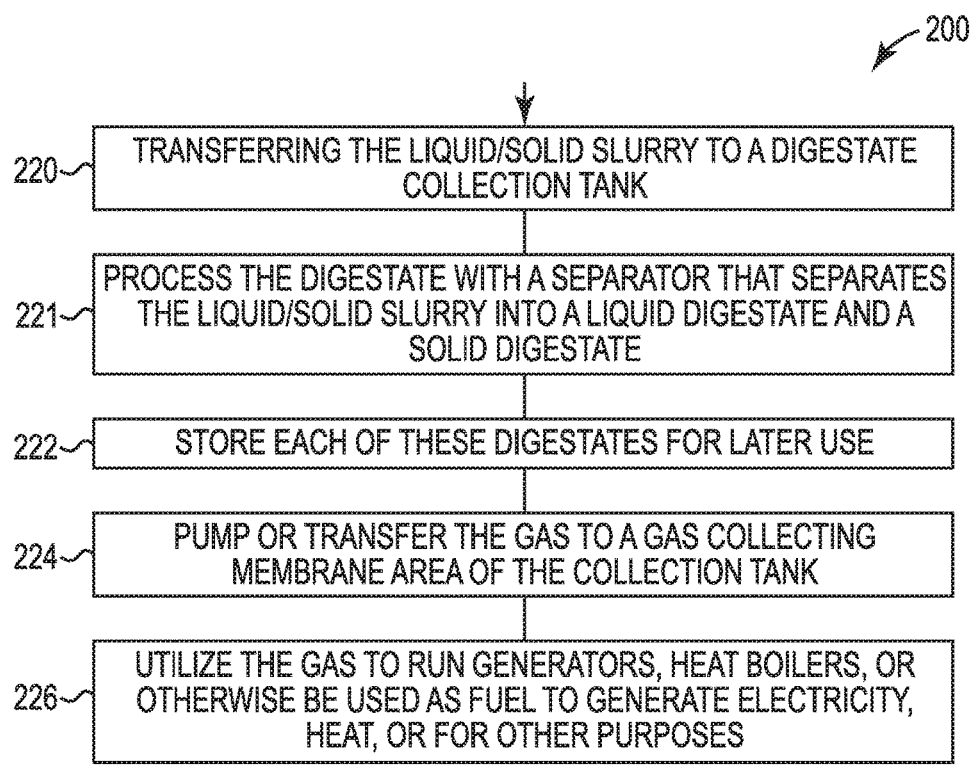
FIG. 15B is a partial flow diagram continuing the method shown in FIG. 15A, according to one or more embodiments.

The above-described system may have the several parts described and may be used to perform a corresponding method 200 as shown in FIGS. 15A and 15B. The method may include feeding feedstock 202 including one or more of woody waste, agricultural waste, human waste, garbage, or other organic waste to a pulping/grinding system together with feedwater 204 such as waste water, manure, or other organically rich liquid. In one or more other embodiments, fresh water, river water, lake water or other water may be provided. It is to be appreciated that the use of waste water may be particularly advantageous due to the often abundant supply and the relatively high organic content, which may help to further the reactions in the anaerobic digestion process by not only adding diluting water but also carbon-rich solids while also processing the waste water.

The pulping/grinding system may be used to cut, slice, tear, or otherwise annihilate or obliterate the structure of the incoming feedstock 206. A catalyst such as magnetite may be added to the feedstock and feedwater material at or around the pulping/grinding portion of the process 208.

The pulped/ground material may be pumped to a hydrolysis tank and hydrolysis may be allowed to occur within the material 210. The liquid/solid slurry may produce gas during the hydrolysis phase and each of the gas and liquid/solid slurry may be transported separately to an anaerobic reactor.

The liquid/solid slurry may be placed in a first anaerobic reactor compartment and the gas from the hydrolysis step may be perfused, bubbled, or otherwise reintroduced into the liquid/solid slurry 212. A process that is the same or similar to acidogenesis may be allowed to occur in the first anaerobic reactor compartment and gas may be generated and collected in the gas release area of the first compartment. The liquid/solid slurry may then move to a second anaerobic reactor compartment and the gas collected in the gas collection area of the first anaerobic compartment may be pumped and perfused, bubbled, or otherwise reintroduced into the liquid/solid slurry in the second compartment 214. A process that is the same or similar to acetogenesis may be allowed to occur in the second anaerobic reactor compartment and gas may be generated and collected in the gas release area of the second compartment. This process may continue through a third anaerobic reactor compartment where the liquid/solid slurry from the second compartment passes to the third compartment and the gas from second compartment is perfused, bubbled, or otherwise reintroduced into the third compartment 216. A process that is the same or similar to methanogenesis may be allowed to occur in the third anaerobic reactor compartment and gas may be generated and collected in the gas release area of the third compartment. Mixing, churning, or otherwise agitating the liquid/solid slurry may occur in one or more of the compartments of the anaerobic reactor 218.

The liquid/solid slurry may exit the reactor and be pumped to a digestate collection tank 220 and it may be further processed with a separator that separates the liquid/solid slurry into a liquid digestate and a solid digestate 221. Each of these digestates may be stored for later use 222. The gas may exit the reactor and be pumped to a gas collecting membrane area of the collection tank 224. The gas may then be used to run generators, heat boilers, or otherwise be used as fuel to generate electricity, heat, or for other purposes 226. In the case of electricity, such may be provided directly to an end user or it may be used to supply power to a power grid for use by one or more users. In the case of heating boilers, the heat may be generated and supplied to one or more users.

The above-described system may be advantageous for several reasons. While previous anaerobic processes have avoided attempts to process woody wastes, the presently disclosed system has shown success in processing these types of materials. The system has shown an ability to breakdown lignin and previous systems have shown an inability to do so. Furthermore, the present system has shown an ability to generate more gas per mass of solid than previous systems through introduction of the catalyst in the hydropulper or grinder. It is believed that the pulping/grinding process provides for a medium and/or multitude of surfaces for microorganisms to reside and destroy the organic solid. The catalyst also helps in reducing $H_2S$ into a lower ppm (part per million or mg per liter), which provides the ability of the biogas to go directly into a generator without harmful damage (corrosion) of the expensive parts of the generator by acid generated from $H_2S$. This is in contrast to existing/present systems that include scrubbers for removal of $H_2S$ from the biogas before sending the gas to a generator. The scrubbers and scrubbing process can be costly. In addition, the present system's re-introduction of gases from one compartment into the next (gas polishing) helps its ability to produce much more gas when compared to known systems. Additional volatile solid reduction of organics and gas generation of the present system is also due to introduction of a hydropulper or grinder. When combined, the current system produces over 50% more gas per mass of dry organics than existing/present systems.

Figure 11:
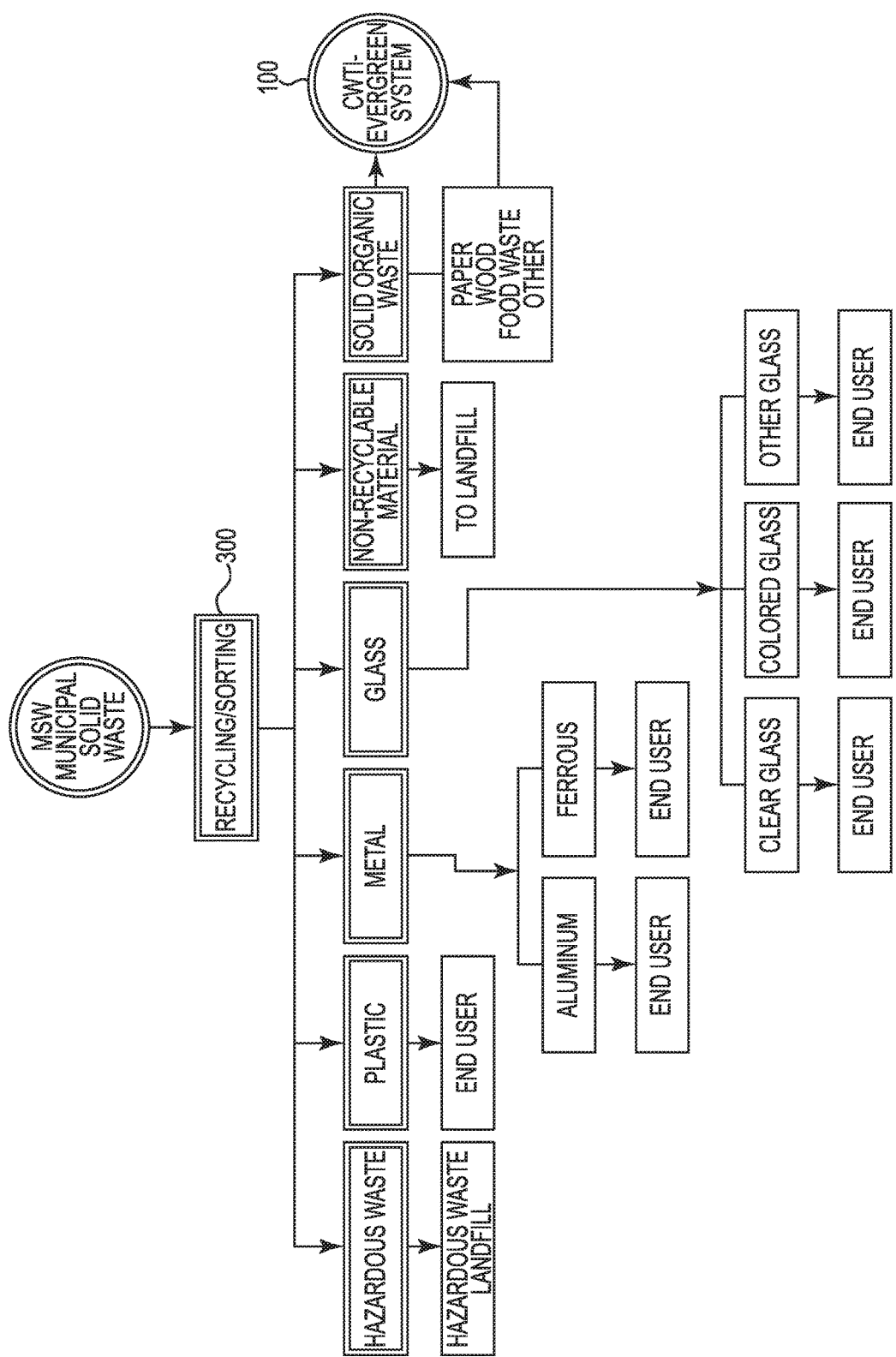
FIG. 11 is a process flow diagram of a municipal solid waste treatment system, according to one or more embodiments.
Figure 12:
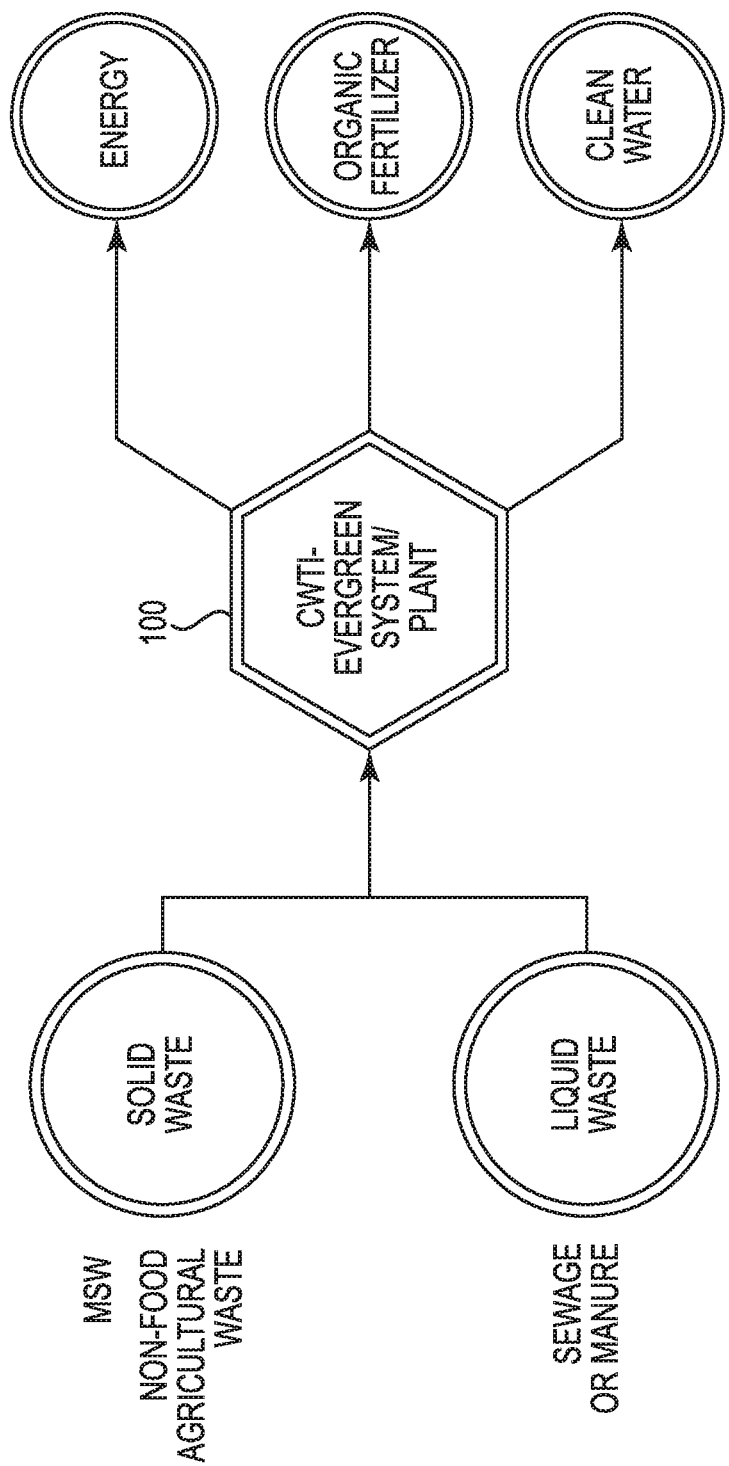
FIG. 12 is a process flow diagram of a municipal solid waste treatment system including a waste water influent portion and a clean water effluent portion, according to one or more embodiments.
Figure 13:
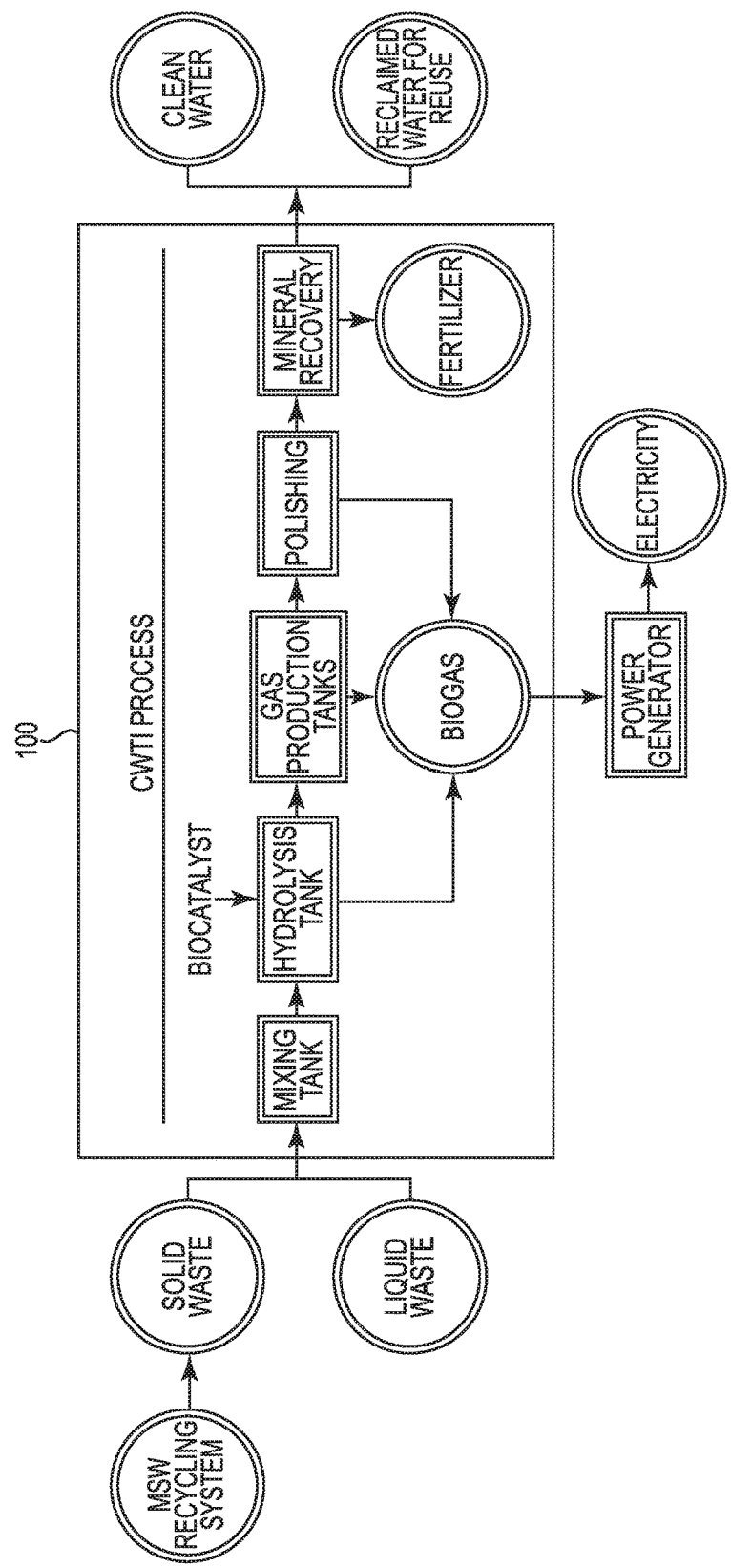
FIG. 13 is a process flow diagram showing a detailed thereof, according to one or more embodiments.
Figure 14:
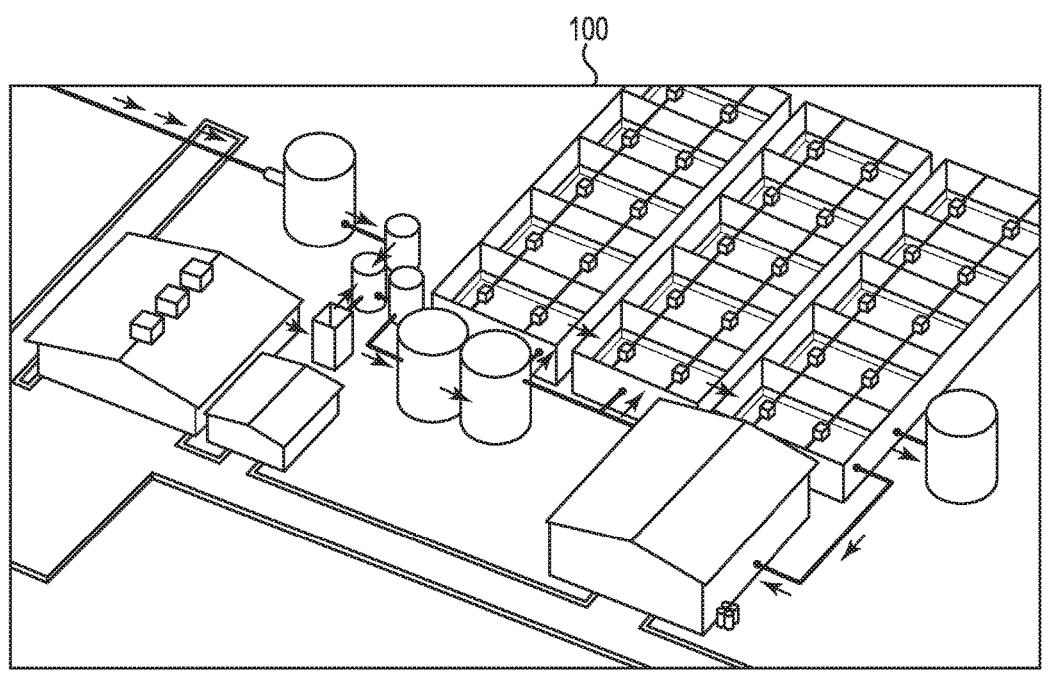
FIG. 14 is a perspective view of an anaerobic digestion system, according to one or more embodiments.

The above-described system may be used as part of a complete waste processing system. For example, as shown in FIG. 11, a municipal solid waste facility may include a recycling/sorting process 300 to remove hazardous waste, plastics, metals, glass, and non-recyclable material. The remaining solid organic waste may be processed by the above-described system. Accordingly, in one or more embodiments, the system may include these associated processes including the initial sorting process and further sorting processes of particular types as shown in the figures. In one or more embodiments, the system may be used in conjunction with and/or may include a waste water treatment facility, where waste water from, for example, a sanitary sewer system is incorporated into the above-described system thereby handling all of a municipalities waste. In one or more embodiments, as shown in FIG. 12, the fluid processing system of the liquid leachate may, in turn, provide water back to the municipality for use and/or consumption. In one or more embodiments, a system such as the one described in U.S. patent application Ser. No. 14/815,130 may be added in front of the system to treat the wastewater and send the concentrate into the current system, and in turn, provide clean water back to the municipality or private consumer for use and/or consumption. A more detailed view of this process is shown in FIG. 13. One example of a system according to the present disclosure is shown in FIG. 14.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. An anaerobic digestion system, comprising:
   a material grinding/pulping portion;
   a hydrolysis portion arranged downstream of the grinding portion;
   an anaerobic reactor arranged downstream from the hydrolysis portion and comprising a plurality of zones each defining a particular stage of an anaerobic digestion process and a gas collection and reintroduction system configured to collect gas from one of the plurality of zones and reintroduce the gas into a downstream zone; and
   a collection system for collecting digestate and gas from the anaerobic reactor.

2. The system of claim 1, further comprising an input system comprising a feedstock input device.

3. The system of claim 2, wherein the input system comprises a liquid feeding system.

4. The system of claim 3, wherein the liquid feeding system comprises a waste water stream.

5. The system of claim 4, wherein the waste water stream is one of animal and human waste water.

6. The system of claim 1, wherein the material grinding/pulping portion comprises a hydropulper.

7. The system of claim 1, wherein the material grinding/pulping portion comprises a hammer mill.

8. The system of claim 1, wherein the material grinding/pulping portion comprises a skimmer.

9. The system of claim 1, wherein the material grinding/pulping portion comprises a catalyst input system.

10. A method of converting waste to energy, comprising:
    receiving and grinding feedstock material to form a liquid/solid slurry;
    performing hydrolysis on the liquid/solid slurry;
    performing anaerobic digestion on the liquid/solid slurry in an anaerobic reactor, the anaerobic reactor comprising a plurality of stages arranged in series; and
    collecting gas from a first stage of the plurality of stages and reintroducing the gas into the liquid/solid slurry in a later stage of the plurality of stages.

11. The method of claim 10, wherein reintroducing the gas includes pumping the gas into a reactor compartment and releasing the gas within the liquid/solid slurry in the later stage.

12. The method of claim 11, wherein reintroducing the gas includes one of perfusing, bubbling, and sparging.

13. The method of claim 10, further comprising feeding the system with waste water.

14. The method of claim 13, wherein the waste water is one of human and animal waste water.

15. An anaerobic digestion system, comprising:
- an input system comprising a feedstock input device and a liquid feeding system, the liquid feeding system comprising a waste water stream;
- a material grinding/pulping portion;
- a hydrolysis portion arranged downstream of the grinding portion;
- an anaerobic reactor arranged downstream from the hydrolysis portion; and
- a collection system for collecting digestate and gas from the anaerobic reactor.

16. The system of claim 15, wherein the waste water stream is one of animal and human waste water.

17. The system of claim 15, wherein the anaerobic reactor comprises a plurality of stages and includes a gas collection and reintroduction system.

18. The system of claim 17, wherein the gas collection system is configured to collect gas from a first stage of the plurality of stages and reintroduce the gas into feedstock material in a later stage of the plurality of stages.

19. The system of claim 15, wherein the material grinding/pulping portion comprises a hydropulper.

20. The system of claim 15, wherein the material grinding/pulping portion comprises a hammer mill.

* * * * *